United States Patent [19]

Steinmetz et al.

[11] Patent Number: 5,233,075

[45] Date of Patent: Aug. 3, 1993

[54] PROCESS FOR THE PREPARATION OF AROMATIC CARBOXYLIC ACID ESTERS

[75] Inventors: Guy R. Steinmetz, Kingsport; Andrew J. Matosky, Johnson City, both of Tenn.

[73] Assignee: Eastman Kodak Company, Rochester, N.Y.

[21] Appl. No.: 776,019

[22] Filed: Oct. 15, 1991

[51] Int. Cl.$^5$ .................. C07C 67/36; C07C 17/00
[52] U.S. Cl. .................. 560/80; 204/157.62; 204/157.87; 204/157.94; 560/97; 560/100; 560/102; 560/103; 570/181
[58] Field of Search .................. 204/157.62, 157.87, 204/157.94; 560/97, 80, 100, 102, 103; 520/181

[56] References Cited

U.S. PATENT DOCUMENTS

| | | | |
|---|---|---|---|
| 2,565,462 | 8/1951 | Prichard et al. | 560/97 |
| 4,649,216 | 3/1987 | Rule et al. | 562/406 |
| 4,778,917 | 10/1988 | Steinmetz et al. | 560/80 |
| 4,778,918 | 10/1988 | Steinmetz et al. | 560/80 |
| 4,780,563 | 10/1988 | Steinmetz et al. | 560/80 |
| 4,803,296 | 2/1989 | Steinmetz et al. | 560/80 |
| 4,806,676 | 2/1989 | Steinmetz et al. | 560/80 |
| 4,827,018 | 5/1989 | Rule et al. | 560/80 |
| 4,847,406 | 7/1989 | Steinmetz et al. | 560/80 |
| 4,851,564 | 7/1989 | Steinmetz et al. | 560/80 |
| 4,866,200 | 9/1989 | Rule et al. | 560/80 |
| 4,904,817 | 2/1990 | Steinmetz | 560/80 |
| 4,912,250 | 3/1990 | Steinmetz et al. | 560/80 |

OTHER PUBLICATIONS

Nakayama et al, *Bull. Chemical Soc.*, Japan 62 (1969), pp. 1124–1129.
K. Suslick, *Science*, 247, (1990), pp. 1439–1445.

*Primary Examiner*—José G. Dees
*Assistant Examiner*—Vera C. Clarke
*Attorney, Agent, or Firm*—Charles R. Martin; William P. Heath, Jr.

[57] ABSTRACT

A process comprising preparing an aromatic carboxylic ester and an alkyl iodide by carboxylating an aromatic iodide in the presence of an alkylating agent and a catalytic amount of a transition metal under aromatic carboxylic ester and alkyl iodide forming conditions of temperature, pressure and ultrasound.

15 Claims, No Drawings

PROCESS FOR THE PREPARATION OF AROMATIC CARBOXYLIC ACID ESTERS

This invention concerns a novel process for the manufacture of aromatic carboxylic acid esters by the carbonylation of aromatic iodides in the presence of ultrasound. More specifically, this invention concerns a process for the co-production of aromatic carboxylic acid esters and alkyl iodides by the carbonylation of aromatic iodides in the presence of a Group VIII metal catalyst, an alkylating agent and ultrasound.

There are numerous processes reported in the literature which involve the production of aromatic carboxylic acid esters by the carbonylation of aromatic iodides in the presence of a metal catalyst.

U.S. Pat. No. 3,988,358 discloses the palladium-catalyzed carbonylation of aromatic halides in the presence of alcohol and a tertiary amine to produce aromatic carboxylic acid esters. Nakayama and Mizoroki disclose in Bull. Chemical Soc. Japan 42 (1969) 1124 the nickel-catalyzed carbonylation of aromatic halides in the presence of an alkanol and potassium acetate to produce aromatic carboxylic acid esters. In these processes, the halide of the aromatic halide reactant is converted to an ammonium salt compound or an alkali salt from which the halogen values cannot be recovered in an economically feasible manner.

U.S. Pat. No. 2,565,462 discloses the carbonylation of aromatic halides in the presence of alkanols, ethers and phenols and a carbonyl of iron, nickel or cobalt. The process described in this patent employs a noncatalytic amount of iron, nickel and cobalt which are used as promoters under severe reaction conditions.

The synthesis of aromatic carboxylic acids and esters by the carbonylation of aromatic iodides in the presence of transition metal catalysts and an alkylating agent, such as an alkanol or an ether, is described in U.S. Pat. Nos. 4,912,250, 4,904,817, 4,866,200, 4,851,564, 4,847,406, 4,827,018, 4,806,676, 4,803,296, 4,780,563, 4,778,918, 4,778,917, and 4,649,216. The presence of an alkylating agent in these processes is advantageous because the iodine values originating from the aromatic iodide reactants may be recovered as alkyl iodides.

Although the processes disclosed in the above group of patents represent commercially viable approaches to production of aromatic carboxylic acids and esters, these reactions generally require moderate to high reaction pressures and temperatures.

We have now discovered a process which has a number of advantages over the prior art. One advantage is that the process of this invention results in the carbonylation of aromatic iodides to aromatic carboxylic esters with a low amount of corresponding carboxylic acid. Another advantage is that the process of this invention results in excellent yields and excellent rates of conversion. Another important advantage is that the process produces alkyl iodides from which the iodine values can be economically recovered. A still further advantage is that the process can be operated at lower temperatures and pressures than the prior art. This advantage is particularly significant because lower temperatures and pressures permit energy savings. Additionally, lower pressures permit less expensive and safer reactors.

Broadly, in the process of this invention an aromatic iodide is carbonylated by contact with gaseous carbon monoxide in the presence of a Group VIII metal catalyst selected from palladium, rhodium, nickel, ruthenium, iridium or mixtures thereof, an alkylating agent and ultrasound.

The use of ultrasound is an essential aspect of the process of this invention. Chemical reactions associated with the presence of ultrasound are thought to involve a phemonemon often referred to as acoustic cavitation. Acoustic cavitation is the formation, growth, and subsequent collapse of bubbles in a liquid. The collapse of the bubbles is thought to generate energy bursts which appear as intense localized temperatures and pressures. The lifetimes of the energy burst are very short which results in only relatively moderate changes in the bulk temperature of the reaction.

It is known in the art that chemical reactions can be conducted in the presence of ultrasound. Examples of such reactions are stoichiometric oxidations and coupling reactions. The sound intensity useful in these reactions can vary widely. Often low intensity ultrasound, such as is emitted from an ultrasonic cleaning apparatus used in a chemistry laboratory, can be used. In other cases, more intense ultrasound can be used. The use of ultrasound in chemical reactions is disclosed by K. Suslick in Science 247 (1990) 1439. U.S. 4,616,096 discloses the use of ultrasound in the preparation of aldehydes.

In this invention the frequency of the ultrasound can range from a few hertz to a few megahertz but preferably is in the range of 15 to 100 kHz. In this invention the acoustic intensity of the ultrasound can range from approximately 1 to 20 $kW/cm^2$.

The aromatic iodides, alkylating agents, Group VIII metal catalysts, the amounts thereof, and the approximate process conditions of pressure and temperature which may be utilized in this novel process are described generally in the U.S. Patents cited above.

The aromatic iodide which may be used in our process may be mono or poly-iodo, e.g. di- tri- and tetra-iodo aromatic compounds. The aromatic nucleus or moiety can contain 18 carbon atoms and may be carbocyclic aromatic such as benzene, biphenyl, terephenyl, naphthalene, anthracene, etc. In addition to one or more iodine atoms, the aromatic moiety amy be substituted by various substituents inert or relatively inert under the conditions employed in our process. Examples of such substituents include alkyl of up to about 12 carbon atoms such as methyl, ethyl, isobutyl, hexyl, 2-ethylhexyl, nonyl, decyl, dodecyl, and the like; cycloalkyl of about 5 to 12 carbon atom such as cyclopentyl, cyclohexyl, 4-butylcyclohexyl, and the like; hydroxy; alkoxy of up to about 12 carbon atoms such as methoxy, ethoxy, propoxy, butoxy, octyloxy, and the like; halogen such as chloro; alkoxycarbonyl of from 2 to about 8 carbon atoms such as methoxycarbonyl, ethoxycarbonyl, butoxycarbonyl, hexyloxycarbonyl, and the like; carboxyl; cyano; alkenyl of 2 to about 12 carbon atoms such as vinyl, allyl, and the like; formyl; alkanoyl of 2 to about 8 carbon atoms such as acetyl, propionyl, butyryl, hexanoyl, and the like; alkanoylamido of 2 to about 8 carbon atoms such as acetamido, butyramido, and the like; aroylamido such as benzamide; alkylsulfonyl of up to about 8 carbon atoms such as methylsulfonyl, hexylsulfonyl, and the like; and methanesulfonamido, butanesulfonamido, and the like.

The preferred reactants are benzene iodides and naphthalene iodides, i.e., mono- and poly-iodo benzenes and naphthalenes and mixtures thereof. Specific examples of the aromatic iodide reactants include iodobenzene, isomers of diiodobenzene, triiodobenzene, iodotoluene, iodophenol, iodoanisole, iodoacetophenone, diiodobiphenyl, chloroiodobenzene, bromoiodobenzene, diiodonaphthalene, triiodonaphthalene and the various isomers of such compounds. The process of this invention is particularly useful for the preparation of benzene dicarboxylic acid esters and naphthalenedicarboxylic acid esters with low acid content and thus the reactants are diiodobenzene, especially 1,3- and 1,4-diiodobenzene and diiodonaphthalene, especially 2,6- and 2,7-diiodonaphthalene. The aromatic iodides and the method of their preparation are well known in the art.

Our process is carried out in the presence of an alkylating agent which is capable of forming an alkyl iodide under the carbonylation conditions. Examples of suitable alkylating agents are ethers, alkanols and mixtures thereof.

Alkanols containing up to about 12 carbon atoms, preferably up to about 4 carbon atoms, may be employed if desired. Examples of the alkanols which may be used include methanol, ethanol, propanol, butanol, pentanol, hexanol, 2-ethylhexanol, octanol, decanol and the like. Methanol is particularly preferred since it is the least expensive and produces methyl iodide which is the most volatile of the alkyl iodides.

Ethers containing up to about 12 carbon atoms, preferably up to about 4 carbon atoms, may be employed if desired. Dimethyl ether is preferable since it is the least expensive and produces methyl iodide which is the most volatile of the alkyl iodies. Examples of other suitable ethers include diethyl ether, dipropyl ether, dibutyl ether, dipentyl ether, dihexyl ether, diheptyl ether, dioctyl ether, didecyl ether, dibenzyl ether, dioxane, anisole, or mixed dialkyl ethers.

Normally, at least one mole equivalent of alkylating agent should be used for each mole equivalent of aromatic iodide reactant. Typically, the alkylating agent, preferably methanol, is present in an amount which is about 50 to 300 mole percent greater than the moles of compounds constituting the aromatic iodide reactant.

The process of this invention may be carried out in the presence of an organic solvent. Examples of such solvents include aliphatic, alicyclic and aromatic hydrocarbons such as benzene, toluene, the xylenes, hexane, heptane, chlorobenzene, ethylene dichloride, methylchloroform, naphthalene, acetic acid, benzoic acid, methyl benzoate and the like. However, the use of such a co-solvent is not essential. The process provided by this invention may also be carried out in the presence of catalytic promoters such as the alkaline and alkaline earth halides as long as they do not interfere with the recovery of methyl iodide. However, the use of such catalytic promoters is not essential for the carbonylation of aromatic iodides.

The Group VIII metal catalyst may be palladium, rhodium, nickel, ruthenium, iridium or mixtures thereof which may be used as the zero-valent metal or in the form of various complexes which can be reduced to an active catalyst. Examples of the compounds which may be used in my process to provide the requisite Group VIII catalyst include palladium acetate, palladium chloride, rhodium trichloride, rhodium tribromide, rhodium triiodide, rhodium acetate, rhodium oxide, dicarbonyl rhodium acetylacetonate, rhodium carbonyl complexes including halide-substituted analogs, nickel acetate, nickel chloride, nickel iodide, ruthenium trichloride, ruthenium tribromide, ruthenium, triiodide, ruthenium acetate, ruthenium acetylacetonate, ruthenium dioxide, ruthenium tetroxide, ruthenium carbonyl complexes such as ruthenium pentacarbonyl, dodecacarbonyltriruthenium and the halide-substituted analogs thereof, iridium trichloride, iridium tribromide, iridium triiodide, iridium acetylacetonate, dodecacarbonyltetrairidium and the phosphine and halide substituted analogs thereof. The catalyst may be deposited on a suitable support or carrier such as carbon, alumina, silica-alumina, barium sulfate or zinc oxide. The preferred Group VIII metal catalyst is palladium.

The catalytically-effective amount of the catalyst can vary substantially depending on a number of factors such as the particular metal used, the reaction conditions, the conversion rate and yield desired, the mode of operation and the like. For example, with reference to the above-described metals as a group, the concentration of the catalytic metal in the reaction mixture may be within the range of about 0.0001 to 10.0 mole percent, preferably 0.001 to 0.500 mole percent, of the moles of aromatic halide reactant. However, in certain modes of operation such as in a continuous process using a fixed-bed catalyst, the amounts of catalyst and reactant present is difficult, if not impossible, to determine.

When the catalyst is palladium it can be present in a concentration of 0.0001 to 1.0 mole percent, preferably 0.001 to 0.25 mole percent, based on the moles of aromatic iodide reactant. Therefore, the total reaction medium has a palladium concentration of about 0.1 to 1000 ppm with a preferred concentration of 1.0 to 250 ppm.

When the catalyst is rhodium, it can be present in a concentration of 0.001 to 10 mole percent, preferably 0.01 to 1.0 mole percent, based on the moles of aromatic iodide reactant. The rhodium concentration in the total reaction medium therefore is in the range of 10 to 10,000 ppm, preferably 100 to 1000 ppm.

The catalytically effective amount of nickel is in the range of 0.001 to 10.0 mole percent and preferably in the range of 0.1 to 2.5 mole percent, based on the medium thus will contain about 1.0 to 10,000 ppm, preferably 1000 to 1000 ppm, nickel.

Ruthenium and iridium may be used in a concentration of 0.01 to 10.0, preferably 0.1 to 1.0, mole percent, based on the moles of aromatic iodide reactant. Therefore, the concentration of ruthenium or iridium in the total reaction medium is about 10 to 10,000 ppm and preferable about 200 to 1000 ppm.

The process of this invention may be carried out in the presence of an inorganic absorbent to remove water if desired. The inorganic absorbent may be selected from silicas, aluminas, aluminophosphates, aluminosilicates, often called zeolites. Zeolites having a wide range of pore sizes such as large pore, e.g., X- and Y-zeolites, medium pore, e.g., ZSM-5 and small pore, e.g., A-zeolites, zeolites with varying ratios of silica to alumina may be used. These zeolites are further characterized by the presence of at least one alkali, alkaline earth, transition metal or lanthanide cation. Examples of such cations include sodium, potassium, rubidium, cesium, magnesium, calcium, palladium, lanthanum and cerium which are exchangeable according to known procedures. The zeolite lattice also can be modified by a large number of tri- and tetra-valent atoms such as by replacing aluminum with boron, iron, chromium, antimony, arsenic and gallium and replacing silicon with germanium, titanium, zirconium and hafnium. Alternatively, the zeolite absorbent may be used in its acidic form wherein the cation sites of the zeolite are replaced by protons, for example, by treating the zeolite with an aqueous solution of an inorganic acid such as hydrochloric or nitric acid. The 3A and 4A zeolites are the preferred absorbents due to their large absorption capacity for water at elevated temperatures and their small pore size which is highly selective for small molecules such as water.

The absorbent can be used in situ or external to the reaction mixture. The amount of absorbent is not critical provided a sufficient amount is present to decrease the amount of water present or formed as a result of the decarbonylation and alkyl iodide-forming reactions to the level desired. The amount of absorbent used is dependent upon the mode of operation but typically is in the range of about 10 to 1000 weight percent based on the total weight of the reaction mixture or crude product mixture. After the absorbent is saturated, it can be removed or isolated from the process and regenerated, for example, by heating the saturated absorbent to desorb the water and other absorbates.

The process of this invention is conducted in the presence of carbon monoxide which may be essentially pure or it may contain other gases such as carbon dioxide, hydrogen, methane and other compounds produced by synthesis gas plants. Normally, the carbon monoxide is at least 90, preferably at least 95, percent pure.

The process is carried out at carboxylic acid ester forming and alkyl iodide-forming conditions of pressure and temperature. The temperature and pressure are interdependent and can vary considerably. While pressures as high as 10,000 psig can be employed, the cost of utilities and equipment required for such a high pressure operation cannot normally be commercially justified. Accordingly, the pressure normally will be in the range of about 50 to 4000 psig with about 100 to 1000 psig being preferred.

The process normally is carried out at a temperature of about 40° to 225° C. although temperatures moderately higher or lower than those mentioned may be used if desired. The preferred temperature range is about 50° to 150° C. Depending upon the level of acoustic intensity, the temperature of the reaction mixture will be elevated above ambient temperatures with no additional external heating. The desired temperature is then a function of both the acoustic intensity and temperature which provides great freedom in controlling a reaction. If the reaction temperature is judged to be too high, the temperature can be reduced by cooling or by operating the reaction with a flow through cell where only a small part of the total reaction mixture is subjected to ultrasound at any one time.

When a polyiodo aromatic compound is used in this carbonylation process, the products obtained include both aromatic polycarboxylic acid esters and partially carbonylated compounds such as iodoaromatic carboxylic acid esters. The relative amounts of partially or completely carbonylated products are dependent on the contact time of the reactants and catalyst under ester forming conditions. However, partially carbonylated compound such as iodoaromatic carboxylic acid esters are useful as intermediates in the preparation of derivatives of aromatic esters such as compounds which may be obtained by nucleophilic displacement reactions wherein the iodo is replaced by various other nucleophiles according to known procedures. Our process is particularly useful for the preparation of dialkyl esters of aromatic dicarboxylic acids such as 1,3- and 1,4-benzenedicarboxylic and 2,6- and 2,7- naphthalenedicarboxylic acid esters. Such diester compounds, such as dimethyl 2,6-naphthalenedicarboxylate, can be reacted with diols to produce high molecular weight polyesters, e.g., poly(ethylene terephthalate) and poly(ethylene naphthalenedicarboxylate), useful in the molding and extrusion of various articles.

The alkyl iodides which are a co-product of this novel process may be used in other chemical process such as in the preparation of carboxylic acids and anhydrides according to known carbonylation procedures. Alternatively, the alkyl iodies can be oxidatively decomposed at elevated temperatures to produce a gaseous mixture of iodine, carbon dioxide and water from which the iodine can be recovered. The iodine also may be recovered by thermal decomposition of the alkyl iodides to iodine and an alkane. The process provided by this invention includes the formation of an alkyl iodide. Thus, the carbonylation reaction is carried out in the absence of any significant amounts of basic materials which preferentially combine with hydrogen iodide to form salts and thus interfere with or prevent the formation and recovery of an alkyl iodide. Examples of such iodide salt-forming bases which are essentially absent form the carbonylation reaction include amines, particularly tertiary amines, and hydroxides, alkoxides and weak acid salts such as carboxylates of the alkali and alkaline earth metals.

Although certain of the inorganic absorbents described hereinabove contain alkali metal cations, such absorbents may be employed by positioning the absorbent, e.g., in the form of absorbent beds, external to the carbonylation reactor in a manner which permits the reactor off-gas to be circulated through the absorbent to selectively remove water from the process effluent and not affect to any significant degree the formation and recovery of an alkyl iodide. A number of the inorganic absorbents may be used within the carbonylation reactor, i.e., in contact with the liquid reaction mixture, without affecting to a significant degree the formation and recovery of an alkyl iodide when the process is operating at steady state. Satisfactory performance of such an internal absorbent depends upon a number of factors such as base strength, pore size and the economic necessity to recover all of the iodide as an alkyl iodide.

The process of this invention results in the preparation of carbonylic acid esters and a low amount of the corresponding free carboxylic acid. The mole ratio of ester groups to acid groups in the crude product obtained from the process is dependent upon the mode of operation and water concentration but typically is at least 5 and preferably at least 20.

The process of this invention can be carried out as a batch, semi-continuous or continuous operation. In the manufacture of dialkyl esters of aromatic dicarboxylic acids in the quantities required for the preparation of polyesters such as those mentioned above, the process will be conducted in a continuous manner. A typical continuous method of operating the process comprises feeding into a mixed pressure vessel a liquid stream of an alkanol such as methanol, another liquid stream composed of an aromatic iodide such as 1,6-diiodonaphthalene, with or without an organic solvent, and the Group VIII metal catalyst and a gaseous stream of carbon monoxide while being subjected to ultrasound. The reaction mixture or its gaseous vapors can be passed through a series of absorbent beds to remove water co-produced in the reaction. These absorbent beds can be isolated independently so that one or more beds can be regenerated in a continuous process. The pressure vessel is equipped with means for maintaining the desired temperature and pressure. The liquid mixture from the reactor is passed to a flash column where the alkyl iodide and organic solvent ma be flashed off. The flashed vapor stream is then condensed and the alkyl iodide and alkanol separated by decanting. The liquid underflow from the flash column is centrifuged and any carboxylic acid is separated from the solution containing the ester of the carboxylic acid. The desired carboxylic acid ester is then recovered by selective crystallization and the remaining mixture containing unreacted aromatic iodide and catalyst is recycled.

The process of this invention is further illustrated by the following examples:

EXAMPLE 1

This example illustrates the process of this invention wherein iodobenzene is carbonylated in the presence of methanol, toluene, palladium acetate, and ultrasound.

Into a 6 ounce aerosol reaction vessel, connected to a cylinder containing carbon monoxide, was added 9.52 grams iodobenzene, 16.20 grams methanol, and 40.0 mL toluene containing 0.0332 grams palladium acetate. The aerosol vessel was suspended in a Branson Model 3200 ultrasonic cleaner filled with water. The ultrasonic cleaner was turned on. The frequency of the ultrasound emitted was about 55 kH. The acoustical intensity was in the range of 1 to 20 kW/cm$^2$. The aerosol vessel was pressurized to approximately 90 psig with carbon monoxide at ambient temperature and vented. This pressurization/vent procedure was repeated nine times. The aerosol vessel was finally pressurized to approximately 90 psig with carbon monoxide and sealed. This point in the procedure represents the beginning of the reaction time. Reactor pressure is maintained by repressurizing the reaction vessel to 90 psig with carbon monoxide if the pressure fell below 85 psig. The carbon monoxide used was essentially pure. After 1.5 hours, a sample was taken. The reaction was repressurized to 90 psig. After 39 hours and 40 minutes, another sample was taken and the reaction vessel was vented. Both samples were analyzed by gas chromatography methods.

The 1.5 hours sample showed a small amount of methyl benzoate and methyl iodide as the only products. The 40 hour sample showed moderate conversions to both methyl benzoate and methyl iodide.

EXAMPLE 2

This example illustrates the process of the invention wherein iodonaphthalene is carbonylated in the presence of methanol, toluene, palladium acetate, and ultrasound.

Example 1 was repeated except that the reaction mixture consisted of 0.412 grams 2,6-diiodonaphthalene, 8.39 grams methanol, and 30.0 mL toluene containing 0.0249 grams palladium acetate and that the reaction time was limited to five hours. The reaction mixture was diluted with toluene to insure that everything was in solution and was then analyzed by gas chromatography methods.

The only products detected were 0.84% 2,6-diiodonaphthalene and 0.02% 2-iodo 6-methylnaphthoate.

EXAMPLE 3

This example illustrates the prior art wherein iodonaphthalene is carbonylated in the presence of methanol, toluene, palladium acetate but without the presence of ultrasound.

Example 1 was repeated except no ultrasound was used, the reaction mixture consisted of 0.219 grams 2,6-diiodonaphthalene, 7.92 grams methanol, and 30.0 mL toluene containing 0.0249 grams palladium acetate, the aerosol vessel was heated to 65° C. to simulate the bulk temperature of the reaction mixture that normally occurs during sonication and the reaction time was five hours. The reaction mixture was diluted with toluene to insure that everything was in solution and was then analyzed by gas chromatography methods.

No carbonylated products were detected. The only product detected was 0.64% 2,6-diiodonaphthalene.

The invention has been described in detail with particular reference to preferred embodiments thereof, but it will be understood that variations and modifications can be effected within the spirit and scope of the invention.

We claim:

1. A process comprising preparing an aromatic carboxylic ester and an alkyl iodide by carbonylating carbon monoxide and an aromatic iodide in the presence of an alkylating agent and a catalytic amount of a transition metal under aromatic carboxylic ester and alkyl iodide forming conditions of temperature, pressure and ultrasound.

2. The process of claim 1 wherein the transition metal is selected from the group consisting of palladium, rhodium, nickel, ruthenium, iridium, and mixtures thereof.

3. The process of claim 1 wherein the aromatic iodide is selected from the group consisting of diiodonaphthalene and diiodobenzene.

4. The process of claim 3 wherein the diiodonaphthalene is 2,6-diiodonaphthalene and the diiodobenzene is 1,4-diiodobenzene.

5. The process of claim 1 wherein the alkylating agent is selected from the group consisting of ethers, alkanols and mixtures thereof.

6. The process of claim 5 wherein the ether or alkanol contains from 1 to 4 carbon atoms.

7. The process of claim 6 wherein the ether is dimethyl ether and the alkanol is methanol.

8. The process of claim 1 wherein the temperature is in the range of 40° to 225° C.

9. The process of claim 8 wherein the temperature is in the range of 50° to 150° C.

10. The process of claim 1 wherein the pressure is in the range of 50 to 4,000 psig.

11. The process of claim 10 wherein the pressure is in the range of 100 to 1,000 psig.

12. The process of claim 1 wherein the ultrasound frequency is in the range of 15 to 100 kHz and the acoustic intensity is in the range of 1 to 20 kW/cm$^2$.

13. The process of claim 1 wherein the process is carried out in the presence of an organic solvent.

14. A process comprising preparing an aromatic dicarboxylic ester selected from the group consisting of dimethyl benzenedicarboxylate and dimethyl naphthalenedicarboxylate and methyl iodide by carbonylating a diiodobenzene or a diiodonaphthalene in the presence of carbon monoxide, methanol, an organic solvent, and a catalytic amount of palladium at a temperature of about 50° to 150° C., a pressure of about 100 to 1,000 psig, an ultrasound frequency of about 15 to 100 kHz, and an ultrasound acoustic intensity of about 1 to 20 kW/cm$^2$.

15. A process comprising preparing 2,6-dimethyl naphthalenedicarboxylate and methyl iodide by carbonylating 2,6-diiodonaphthalene in the presence of carbon monoxide, methanol an organic solvent and a catalytic amount of palladium at a temperature of about 50° to 150° C., a pressure of about 100 to 1,000 psig, an ultrasound frequency of about 15 to 100 kHz, and an ultrasound acoustic intensity of about 1 to 20 kW/cm$^2$.

* * * * *